United States Patent [19]

Senyei et al.

[11] Patent Number: 5,096,830
[45] Date of Patent: Mar. 17, 1992

[54] PRETERM LABOR AND MEMBRANE RUPTURE TEST

[75] Inventors: Andrew E. Senyei, Santa Ana; Nelson N. H. Teng, Hillsborough, both of Calif.

[73] Assignee: Adeza Biomedical Corporation, Sunnyvale, Calif.

[21] Appl. No.: 244,969

[22] Filed: Sep. 15, 1988

Related U.S. Application Data

[63] Continuation-in-part of Ser. No. 121,895, Nov. 17, 1987, abandoned, and Ser. No. 121,899, Nov. 17, 1987, abandoned.

[51] Int. Cl.$^5$ .............................................. G01N 33/48
[52] U.S. Cl. ........................................ 436/65; 436/63; 436/510; 436/518; 436/547; 436/548; 436/814
[58] Field of Search .................... 435/7; 436/510, 518, 436/547, 548, 63, 65, 814

[56] References Cited

U.S. PATENT DOCUMENTS

| | | | |
|---|---|---|---|
| 3,271,257 | 9/1966 | Averette, Jr. ................ | 167/84.5 |
| 4,279,992 | 7/1981 | Boguslaski et al. ............... | 435/7 |
| 4,675,286 | 6/1987 | Calenoff ............................ | 435/7 |

FOREIGN PATENT DOCUMENTS

| | | |
|---|---|---|
| 60-091264 | 5/1985 | Japan . |
| 1107051 | 8/1984 | U.S.S.R. . |

OTHER PUBLICATIONS

Oellevich, M., J. Clin. Chem. Clin. Biochem., vol. 22(12), pp. 895–904 (1984).
*The New England Journal of Medicine:* vol. 325, No. 10, 669–674 (1991) "Fetal Fibronectin in Cervical and Vaginal Secretions as a Predictor of Preterm Delivery", by Lockwood et al.
*Int. J. Caner:* 27, 763–767 (1981) "Fibronectin from Human Germ-Cell Tumors Resembles Amniotic Fluid Fibronectin", by Ruoslahti et al.
Gahl et al., *Obstet. Gynecol.* 60: 297–304 (1982).
Koninckx et al., *Br. J. Obstet. Gynaecol.* 88: 607–610 (1981).
Huber et al., *Br. J. Obstet. Gynaecol.* 90(12): 1183–1185 (1983).
Phocas et al., *Eur. J. Obstet. Gynecol. Reprod. Biol.* 31: 133–141 (1989).
Ali, E. et al., *J. Biol. Chem.* 256: 7671–7677 (1981).
Anonymous, *Ob/Gyn Topics* 2: 5 (1987).
Anonymous, *Ob. Gyn. News* (Dec. 31, 1987).
Anunciado, A. et al., *Am. J. Obstet. Gynecol.* 156: 898–890 (1987).
Atlay, R. et al., *Amer. J. Obstet. Gynec.* 108: 993–994 (1970).
Azzarone, B. et al., *Int. J. Cancer* 38: 177–181 (1986).
Bala, S. et al., *Aust. NZ. J. Obstet. Gynecol.* 26: 141–144 (1986).
Barnea, E. et al., "β-HCG and Other Chemical Parameters of Ectopic Pregnancy", Maryland: Aspen Publishers, Inc. (1986).
Bartal, A. et al., *JNCI* 76: 415–419 (1986).
Bell, S. *Human Reproduction* 1: 129–143 (1986).
Bergeron, C. et al., *Contemporary Ob/Gyn* 55–66 (1987).
Bhatia, R. et al., *Am. J. Obstet. Gynecol.* 157: 106–108 (1987).
The Human Placenta, Boyd, J. et al., New York: MacMillan Press (1970).
Bray, B., *Biochem. J.* 226: 811–815 (1985).
Bulmer, J. et al., *Placenta* 6: 127–140 (1985).
Bützow, R. et al., *Human Reproduction* 1: 287–289 (1986).
Cossu, G. et al., *J. Biol. Chem.* 258: 5603–5607 (1983).
Dodds, W. et al., *J. Reprod. Med.* 32: 527–530 (1987).
Friedman, M. et al., *Am. J. Obstet. Gynecol.* 104: 544–550 (1969).
Ganrot, P., *Scand. J. Clin. Lab. Invest.* 29: 83–88 (1972).
Hayashi, M. et al., *J. Biol. Chem.* 256: 11292–11300 (1981).
Hess, L., *Obstet. Gynecol.* 68: 25–28 (1986).
Immunoassays for the 80s, Voller et al. (ed.), Baltimore: University Park Press (1981).
Johnson, P. et al., *J. Immunol.* 132: 1608–1610 (1984).
Kiyotoshi, S. et al., *Biochem. Biophys. Res. Comm.* 116: 534–540 (1983).
Kuusela, P. et al., *Scand. J. Immunol.* 12: 331–337 (1980).
Leveno, K. et al., "Dilemmas in the Management of Preterm Birth, Part One, Pregnancies at Risk", Williams Obstetrics Supplement, 12, May/Jun. 1987.

(List continued on next page.)

*Primary Examiner*—Sam Rosen
*Attorney, Agent, or Firm*—Skjerven, Morrill, MacPherson, Franklin & Friel

[57] ABSTRACT

A method for determining increased risk of labor and fetal membrane rupture after week 20 of pregnancy comprises obtaining a secretion sample from the vaginal cavity; and determining the presence of a fetal restricted antigen in the sample. The sample can be removed from anywhere in the vaginal cavity, but is preferably removed from the posterior fornix or and/or cervical os. One fetal restricted antigen is fetal fibronectin. In one embodiment of this invention, the sample is contacted with an insoluble support to which anti-(fetal restricted antigen) antibody is adhered, and the fetal restricted antigen binding to the support is determined. Alternatively, the class of substances of which the fetal restricted antigen is a member is captured with a general binding antibody (such as anti-human fibronectin antibody), anti-(fetal restricted antigen) antibody (such as anti-fetal fibronectin antibody) is conjugated with the support, and binding with fetal restricted antigen is determined.

Reagents and reagent kits are also included.

14 Claims, No Drawings

OTHER PUBLICATIONS

Matsuura, J. et al., *Proc. Natl. Acad. Sci. U.S.A.* 82: 6517–6521 (1985).

McCoshen, J., *Contemporary Ob/Gyn* May, 1987: 94–117.

McSweeney, D. et al., *Fertility and Sterility* 18: 866–869 (1967).

Murayama, K. et al., *Gylcoconjugate* 1: 155–169 (1984).

Sandler, S. et al., *S. A. Medical Journal* Sep., 1977: 487–492.

Sbarra, A. et al., *Obstet. Gynecol.* 70: 107–110 (1987).

Sinosich, M. et al., *Obstet. and Gynecol.* Survey 40: 273–282 (1985).

Stubbs, T. et al., *Am. J. Obstet. Gynecol.* 155: 829–834 (1986).

Wagner, D. et al., *J. Biol. Chem.* 256: 11708–11715 (1981).

Yuen, H., "Clinical Applications of the HCG-$\beta$ Subunit Assay in Obstetrics and Gynecology", Current Problems in Obstetrics, Gynecology and Fertility, Chicago: Year Book Medical Publishers, Inc., (Sep. 1985).

Zhu, B. et al., *J. Biol. Chem.* 259: 3962–3970 (1984).

PRETERM LABOR AND MEMBRANE RUPTURE TEST

RELATIONSHIP TO COPENDING APPLICATIONS

This application is a continuation-in-part of Applications Ser. No. 121,893 filed Nov. 17, 1987 and Ser. No. 121,899 filed Nov. 17, 1987, both now abandoned.

FIELD OF THE INVENTION

This invention relates to methods, reagents and kits for detection of preterm labor and rupture of the amniotic membrane after week 20 of pregnancy. In particular, this invention is directed to the determination of preterm labor and/or rupture of the amniotic membrane of humans by testing cervical and/or posterior fornix samples for the presence of a fetal restricted antigen.

BACKGROUND OF THE INVENTION

Determination of impending preterm births is critical for increasing neonatal survival of preterm infants. Traditional methods of diagnosis of preterm labor have high false-negative and false-positive rates as reported by Friedman, M. et al, *Am.J.Obstet.Gynecol.* 104:544 (1969). In addition, traditional methods may be open to subjective interpretation, require sophisticated training or equipment as reported by Garl, W. et al, *Obstet.-Gynecol.* 60:297 (1982) or be invasive as stated by Atlay, R. et al, *Am.J.Obstet.Gynecol.* 108:933 (1970).

Detection of rupture of the amniotic membrane is important in distinguishing true and false labor, and when the rupture is small and the volume of amniotic liquid escaping is small, the rupture is often undetected. Accepted methods for detecting ruptured membranes such as pooling, nitrazine and ferning are not reliable, being subjective, not sufficiently sensitive and not specific.

Amniotic fluid infections have been associated with both preterm labor with intact membranes and premature rupture of membranes by Leveno, K. et al, "Dilemmas in the Management of Preterm Birth, Part One. Pregnancies at Risk", WILLIAMS OBSTETRICS SUPPLEMENT, 12., Phil.: Wyeth Laboratories and Simon & Schuster pp 1-11 (May/June 1987), and is a major cause of perinatal morbidity and mortality. The possibility that bacterial growth reduces the bursting pressure of fetal membranes in vivo has been confirmed by in vitro studies by Sbarra, A., et al, *Obstet.Gynecol.* 70:107-110 (1987).

DESCRIPTION OF THE PRIOR ART

Traditional methods for differentiation of true and false labor is often difficult before the uterus has contracted sufficiently to produce demonstrable cervical effacement or dilatation. Other traditional signs and symptoms indicating risk of preterm delivery are passage of cervical mucus, often slightly bloody, low backache, pelvic pressure due to descent of the fetus, menstrual-like cramps, and intestinal cramping with or without diarrhea. The traditional approaches are described by Leveno, K (supra) and Stubbs, T. et al, *Am.J.Obstet.-Gynecol.* 155:829-834 (1986).

Several tests have been reported for diagnosis of preterm rupture of membranes. Rochelson, B. et al, *Obstet.Gynecol.* 69:163-165 (1987) reported a rapid, colorimetric monoclonal alpha-fetoprotein (AFP) antibody test, based on the presence of high levels of AFP in amniotic fluid. However, in the case of bloody specimens, the AFP test could be unreliable since maternal blood contains AFP. Huber, J. et al, *Obstet.Gynecol.* 80:1183 (1983) reported that a quantitative AFP radioimmunoassay in the diagnosis of premature rupture of membranes gave too much overlap with non-ruptured controls.

An investigation of the sources, compartmental distribution and clinical significance of a variety of secretarial endometrial and decidual maternally derived group of pregnancy-associated serum proteins such as AFP, chorionic gonadotropin (hCG), human placental lactogen (hPL), pregnancy-associated plasma protein A (PAPP-A), placental protein 5 (PP5), placental protein 10 (PP10), placental protein 12 (PP12), placental protein 14 (PP14), prolactin, $\alpha_2$-globulin ($\alpha_2$-PAG), pregnancy specific $\beta_1$-glycoprotein (SPI) and diamine oxidase (DAO) was reviewed by Bell, *S. Human Reproduction.* 1:129-143 (1986). DAO was thought to be possibly useful in the diagnosis of ruptured fetal membranes where enzyme activity is measured in the vaginal fluid.

Dodds, W. et al, *J.Reprod.Med.* 32:527-530 (1987) reported a study of maternal serum C-reactive protein (CRP) in clinically non-infected preterm labor patients. Women with any chronic or recent illness known to elevate CRP, such as rheumatoid arthritis or acute respiratory infection, were excluded from the study, and this approach does not distinguish risks of preterm labor from CRP levels derived from CRP-elevating infections.

A method for testing for ruptured fetal membranes comprising staining a vaginal smear with a dye capable of enabling vernix caseosa cells to be identified under a microscope is described in U.S. Pat. No. 3,271,257.

In normal pregnancy there is usually no ferning. When the amniotic membrane is ruptured, however, during a sterile speculum examination, pooling of fluids is observed, and ferning and nitrazine tests will be positive. The pooling observation is subjective. The ferning assay (drying of the sample on a slide and observation of the ferning pattern) and the nitrazine test (pH paper) are crude and non-specific. Cervical mucus, urine, semen or blood in the sample could give false results. There is therefore a perceived need for a better determination of ruptured amniotic membranes.

Evolution of the structure and distribution of 4F2-antigen from the oncofetal to the adult phenotype of human fibroblasts has been reported by Azzarone, B. et al, *Int.J.Cancer.* 38:177-181 (1986).

Matsuura, H. and Hakomori, S., *Proc.Natl.Acad.-Sci.USA.* 82:6517-6521 (1985) describe the discovery of a fetal fibronectin which binds preferentially with a monoclonal antibody FDC-6, and that this antibody does not bind preferentially with adult plasma fibronectins. The fetal fibronectin was found in placenta, amniotic fluid and fetal connective tissue, as well as a number of tumors. Structural differences between the fetal fibronectin and adult fibronectins were described. Other references relating to this discovery are Ali, I. et al, *J.Biol.Chem.* 256:7671-7677 (1981); Wagner, D. et al, *J.Biol.CHem.* 256:11798-11715 (1981); Dekiguchi, K. and Hakomori, S., *J.Biol.Chem.* 258:3967-3973 (1983); Hayashi, M. et al, J.Biol.Chem. 256:11292-11300 (1981); Atherton, B. et al, Cell. 25:133-141 (1981); Ruoslahti, E. et al, *Int.J.Cancer.* 27:763-767 (1981); Zhu, B. et al, *J.Biol.Chem.* 259:3962-3970 (1984); Cossu, G. et al, *J.Biol.Chem.* 258:5603-5607 (1983); Murayama, K., Hakomori, S. et al, *Glyconconjugate*. 1:155–169 (1984); Teng, M. et al, *J.Cell.Biol.* 80:784–791 (1979); Liu, M. et al, *Proc.Natl.Acad.Sci.* 82:34–37 (1985); Kiyotoshi, S., Hakomori, S. et al, *Biochem.Biophys.Res.Comm.* 116:534–540 (1983); Sekiguchi, K., Hakomori, S., et al, *J.Biol.Chem.* 260:5105–5114 (1985); Zardi, L., et al, *Int.J.Cancer.* 25:325–329 (1980); and Nakabayashi, H. et al, *Cancer Res.* 42:3858–3863 (1982); Dot, *I. Gann.* 67:1–10 (1976).

Kuusela, P., et al, *Scand.J.Immunol.* 12:331–337 (1980) also disclose a monoclonal antibody binding preferentially with amniotic fluid fibronectin (fetal fibronectin) and a method for preparing the hybridoma therefor. Their antibody, however, binds adult plasma fibronectin with a high level of cross-reactivity.

Immunoassay reagents and procedures have been developed for determining the presence and amount of a wide variety of antigenic and non-antigenic materials in diverse body fluids and tissues. These fall into a broad classification of homogeneous and heterogeneous methods, and are summarized in U.S. Pat. No. 4,279,992 and in IMMUNOASSAYS FOR THE 80s. Voller, A. et al (editors), Baltimore: University Park Press (1981). ELISA immunoassays are described by Maggio, et al, ENZYME-IMMUNOASSAY. Boca Raton: CRC Press pp 172–176 (1980).

A representative listing of known fetal antigens and known antibodies which bind selectively or preferentially therewith are set forth in PREGNANCY PROTEINS: BIOLOGY, CHEMISTRY AND CLINICAL APPLICATION. Grudzinskas, J. et al (editors), New York: Academic Press (1982) and the publications cited therein, the entire contents of which and the publications cited therein being hereby incorporated by reference in their entireties. Examples of identified fetal antigens are chorionic gonadotropin (hCG), human chorionic thyrotropin (hCT), human placental lactogen (hPL), Schwangerschafts-spezifizisches glykoprotein 1 or pregnancy specific $\beta_1$-glycoprotein (SP1), pregnancy-associated plasma protein A (PAPP-A), pregnancy-associated plasma protein B (PAPP-B), heat-stable alkaline phosphatase (HSAP) (S, I, and F phenotypes), cystine aminopeptidase (CAP), placental protein 5 (PP5), placenta specific $\alpha_1$-microglobulin (PAMG$_1$), placenta specific $\alpha_2$-microglobulin (PAMG$_2$), pregnancy associated $\beta_1$-macroglobulin ($\beta_1$-PAM), pregnancy associated $\alpha_2$-macroglobulin ($\alpha_2$-PAM), human chorionic luteinising hormone-releasing factor (hCLRF), human chorionic thyrotropin-releasing hormone (hCTRH), human chorionic growth hormone-releasing inhibiting hormone (somatostatin), all of these being fetal proteins which have been well characterized, purified, and are produced by the placenta. These unrestricted pregnancy antigens are compounds and substances found in significant amounts in the maternal plasma and serum and are not fetal restricted antigens.

Isolation and diagnostic examination of fetal cells from cervical samples obtained by lavage of the uterine cavity is described in U.S. Pat. No. 4,675,286.

An immunological method for determining total fibronectin in samples is described in Japanese Patent Application 60091264 (DIALOG database file 351, WPI Acc. No. 85-161617/27). A non-immunological method is described in USSR Patent Application No. 1107051 (DIALOG database file 351, WPI Acc. No. 85-055390/09). Separation of total fibronectin (also identified as $\alpha_2$-sb-glycoprotein, cold-soluble protein and LETS-protein) by affinity chromatography is described in U.S. Pat. No. 4,325,867.

ATCC HB 91 (American Type Culture Collection, Rockville, MD) is a hybridoma clone which produces an anti-(cellular and plasma fibronectin) antibody.

SUMMARY OF THE INVENTION

The method for determining fetal membrane rupture or an increased risk of preterm birth during pregnancy comprises obtaining a sample from the posterior fornix and/or cervix os; and determining the presence in the sample of a fetal restricted antigen which is not found in significant amounts in maternal plasma or serum.

Since the fetal restricted antigen is not present in significant quantities in maternal plasma or serum, the methods of this invention are reliable even when the sample is contaminated with maternal blood.

The sample can be removed from anywhere in the vaginal cavity, but is preferably removed from the posterior fornix and/or cervical canal. One fetal restricted antigen is fetal fibronectin. In general, these methods comprise interacting the fetal restricted antigen in a sample with an anti-(fetal restricted antigen) antibody for a time sufficient to permit antigen-antibody binding to occur; and determining the presence or absence of said binding. This method can be carried out as a sandwich or competition immunoassay.

In one sandwich embodiment of this invention, the sample is contacted with an insoluble support to which anti-(fetal restricted antigen) antibody is adhered for a time sufficient to permit antigen-antibody binding to occur, and the sample is removed from the support. The insoluble support is then contacted with an antibody which binds with the fetal restricted antigen or the fetal restricted antigen class (i.e., a secondary antibody) for a time sufficient to permit antigen-antibody binding to occur, and the unbound secondary antibody is removed from the support. The presence of secondary antibody on the insoluble support is then determined. The secondary antibody can have a physically detectable label which can be measured directly on the insoluble support. Alternatively, the secondary antibody can be unlabeled, and the secondary antibody can be determined by contacting the insoluble support with a labeled antibody which binds selectively with the secondary antibody (i.e., a tertiary antibody), removing unbound labeled tertiary antibody from the support, and determining the presence of the label on the insoluble support.

In an alternate embodiment of this invention, the sample is contacted with an insoluble support to which is adhered an anti-(fetal restricted antigen class) antibody for a time sufficient to permit antigen-antibody binding to occur and removing the sample from the support. The insoluble support is then contacted with an anti-(fetal restricted antigen) antibody or a preferentially binding fragment thereof for a time sufficient to permit antigen-antibody binding to occur and removing unbound anti-(fetal restricted antigen) antibody from the support. Finally, the presence of anti-(fetal restricted antigen) antibody (or fragment thereof) on the insoluble support is determined. The anti-(fetal restricted antigen) antibody (or fragment) can have a physically detectable label, in which event, the label adhering to the insoluble support can be determined. Alternatively, anti-(fetal restricted antigen) antibody can be unlabeled, and the insoluble support can be contacted with a labeled secondary antibody which binds selectively with the anti-(fetal restricted antigen) antibody, the unbound labeled antibody is removed from the support, and the presence of the label on the insoluble support is determined.

Preterm labor and premature amniotic membrane rupture testing reagents include insoluble supports to which are adhered anti-(fetal restricted antigen) antibodies such as anti-(fetal fibronectin) antibodies, anti-(fetal restricted antigen class) antibodies such as anti-(total fibronectin) antibodies, preferentially binding fragments thereof, and the like.

This invention also includes kits comprising one of the above insoluble support reagents, alone or in combination with labeled antibodies. One preferred embodiment of a kit of this invention comprises an anti-(fetal fibronectin) antibody adhered to an insoluble support (for example, with goat-antimouse antibodies) in combination with a labeled anti-fibronectin antibody. Another preferred embodiment of a kit of this invention comprises an anti-fibronectin antibody (or binding fragment thereof) adhered to an insoluble support, in combination with a labeled anti-(fetal fibronectin) antibody. The reagents can be present in any suitable form in the kit, for example in containers, packages, and the like.

DETAILED DESCRIPTION OF THE INVENTION

The method of this invention involves the detection of uniquely fetal or placental restricted material in a cervical mucus sample. We have discovered that detectable amounts of these materials are generally absent from samples obtained from the posterior fornix and/or cervical canal or os after week 20 of pregnancy, and detectable amounts of these materials present in such samples taken after week 20 pregnancy indicate an increased risk of impending preterm birth or indicate the rupture of the amniotic membrane.

Since the fetal restricted antigens are not present in significant quantities in the maternal blood, the presence of maternal blood in the sample does not interfere with the test.

The term "fetal restricted antigen" as used hereinafter is defined to mean this uniquely fetal or placental derived material, which is either not present in maternal serum, plasma or urine, or is not present in significant amounts in maternal serum, plasma or urine. Any substance meeting this definition is intended to be included within the meaning of the term, including both antigenic materials and proteins and other substances which are not antigenic in their purified form but which have unique epitopes which can be selectively bound with antibodies which have preferential binding properties therewith. An example of a fetal restricted antigen is the fetal fibronectin which binds preferentially with the FDC-6 monoclonal antibody described by Matsurra, H. and Hakomori, S., *Proc.Natl.Acad.Sci.USA.* 82:6517–6521 (1985).

The term "fetal restricted antigen class" as used herein is defined to mean the class or group of antigens of which the "fetal restricted antigen" is a member. For example, fetal fibronectin is a fetal restricted antigen member of the total fibronectin group or class.

The term "unrestricted pregnancy antigen" as used herein is defined to mean compounds or substances which can be detected in body fluids such as serum, plasma, urine or mucus to indicate pregnancy and which are present in significant amounts in maternal serum, plasma or urine.

The term "antibody" as used herein is defined to include antibodies of classes IgG, IgM, IgA, IgD, and IgE, and binding fragments, half-antibodies, and hybrid derivatives of antibodies including, but not limited to Fab, and F(ab')$_2$ fragments of antibodies.

The term "preferentially binding" as used herein is defined to include antibodies and fragments thereof which have less than 10 percent and preferably less than 5 percent cross-reactivity.

In the method of this invention, a sample is removed from an area within the vaginal cavity such as the posterior fornix, cervical canal or uterine cavity, and the sample is examined to determine the presence or quantity of a fetal restricted antigen component, usually a protein such as fetal fibronectin, in the sample. The sample is removed with a swab having a dacron or other fibrous tip, aspirator, suction device, lavage device or the like and transferred to a suitable container for storage and transport to the testing laboratory. It is important that the sample be dispersed in a liquid which preserves the sensitive protein analytes such as fetal fibronectin which are unstable in the sampled composition. The storage and transfer medium should prevent decline in the protein analyte level during storage and transport. A suitable preserving solution for storage and transfer is described in U.S. Pat. No. 4,914,889, the entire contents of which are hereby incorporated by reference in its entirety.

This detection can be achieved by binding fetal restricted antigen in a sample obtained from the vaginal cavity and preferably the posterior fornix, uterine cavity or cervical os with an antibody which binds preferentially with an epitope of the fetal restricted antigen, and determining the presence of this binding. Immunological methods are most convenient for carrying out this method because of their specificity, and the term "immunoassays" as used herein is defined to mean methods using a preferential binding property of a fetal restricted antigen with a second material, a binding partner, usually an antibody or another substance having an antigen binding site which binds selectively and preferably preferentially with an epitope of the fetal antigen. Included within the scope of this invention are all immunoassay methods including this step, including but not limited to sandwich, competition, agglomeration, precipitation, transistor bridge probe, particle sorting, light disturbing, light scattering, and ultrasonic probe immunoassays, for example. Appropriate immunoassays may use, as labels, radioisotopes, enzymes, or fluorogenic, chromogenic, or chemiluminescent substances.

In one preferred embodiment of this invention, the sample is contacted with an insoluble support to which anti-(fetal restricted antigen) antibody is adhered to effect binding and capture of fetal restricted antigen in the sample. The insoluble support is then contacted with an unlabeled or labeled antibody which binds with the fetal restricted antigen adhering to the insoluble support to label and measure the captured fetal restricted antigen. For example, anti-(fetal fibronectin) antibody can be adhered to the insoluble support, and labeled or unlabeled anti-(adult plasma fibronectin) antibody can be used to distinguish the captured antigen.

In another preferred embodiment, the sample is contacted with an insoluble support to which is adhered anti-(adult plasma fibronectin) antibody. The insoluble support is then contacted with the labeled or unlabeled fetal fibronectin antibody which binds with the fetal restricted antigen adhering to the insoluble support, and the captured fetal restricted antigen is determined or measured.

In another embodiment, the sample is contacted with an insoluble support to which is adhered an antibody which captures either the specific fetal restricted antibody or a non-specific group of substances which include the fetal restricted antibody. After being contacted with the sample, the insoluble support is contacted with an unlabeled or labeled antibody which binds with the fetal restricted antigen adhering to the insoluble support, and the captured fetal restricted antigen is measured. For example, anti-(fetal fibronectin) antibody can be adhered to the insoluble support, and labeled or unlabeled anti-(adult plasma fibronectin) antibody can be used to distinguish the captured antigen.

This invention will be described hereinafter with respect to fetal fibronectin, for purposes of clarity, and not by way of limitation, and the detection of any fetal restricted antigen is intended to be within the scope of this invention.

The anti-(fetal restricted antigen) antibody can be obtained from fetal antigens, preferably from highly purified fetal antigens, by conventional antiserum (polyclonal) or monoclonal techniques. Anti-(fetal fibronectin) antibody can be derived from fetal fibronectin by conventional antiserum (polyclonal) techniques or by monoclonal antibody techniques.

Polyclonal anti-(fetal restricted antigen) antibody can be obtained by immunizing an animal such as a rabbit, guinea pig, rat or goat with concentrated fetal restricted antigen, such as fetal fibronectin, removing serum from the immunized animal, and separating the immunoglobulins from the serum, for example by ammonium sulfate precipitation. The principal antibodies useful in the method of this invention are IgG and IgM antibodies, although the IgD, IgE and IgA antibodies can also be used if available in sufficient quantity. The fetal fibronectin antibodies are then affinity purified using conventional affinity chromatography techniques such as those described by Mishell and Shilgi in SELECTED METHODS IN CELLULAR IMMUNOLOGY. San Francisco: Freeman (1980), Goding, J., MONOCLONAL ANTIBODIES: PRINCIPLES AND PRACTICE. New York: Academic Press pp 111-114 (1983), and Parikh, I., et al, E&EN (Aug. 26, 1985), the entire contents of each of which are hereby incorporated by reference. Suitable absorbency for use in affinity chromatography include cross-linked agarose and cross-linked polyacrylamides to which the fetal restricted antigen antibody is covalently bound. For removal of antibodies cross-reacting with adult plasma fibronectins, the antibody serum is passed through columns to which are coupled adult plasma fibronectins. A portion of the eluant containing the remaining antibody can then be passed through a fetal fibronectin column and eluted to yield the affinity purified antibody.

In these procedures, the antibody solution can be applied to the column in a phosphate buffered saline solution, and the antibodies can be eluted with a 2.5 M NaSCN solution, pH 8.0. Antibody concentration, if desired, can be achieved by negative pressure dialysis or ultrafiltration. Repetition of this procedure may be required to achieve the desired purity. Repetition of the column separation procedures is continued until the desired separation and purity is achieved.

Monoclonal anti-(fetal antigen) antibody can be obtained by the methods of Glafre and Milstein, *Methods of Enzym.* 73:1 (1981), immunizing mice with fetal restricted antigens to obtain the spleen cells for hybridization. Suitable procedures are described by Goding, J. (supra, pp 56-97), the entire contents of which are hereby incorporated by reference. For production of fetal fibronectin, the procedures described by Matsuura, H. and Hakomori, S. (supra) can be followed, replacing the tumor fibronectin with fetal fibronectin.

Anti-(fetal restricted antigen class) antibodies of both polyclonal and monoclonal varieties are generally well known and available either commercially or from publicly available hybridoma deposits. For example, anti-(total fibronectin) monoclonal antibodies can be derived from clone samples from ATCC HB 91 (American Type Culture Collection, Rockville, MD). Such antibodies are also described in Japanese Patent Application 60091264 (DIALOG database file 351, WPI Acc. No. 85-161617/27) and U.S. Pat. No. 4,325,867.

The preferentially binding antibody fragments suitable for use in the device, kit and method of this invention can be made from the respective monoclonal or polyclonal antibodies by conventional enzyme or chemical fragmentation procedures. Suitable procedures are described by Tijssen, P. LABORATORY TECHNIQUES IN BIOCHEMISTRY AND MOLECULAR BIOLOGY: PRACTICE AND THEORIES OF ENZYME IMMUNOASSAYS. New York: Elsevier (1985), for example.

The antibody reagents can be bonded to an insoluble support by conventional processes. Procedures for binding of antibodies to insoluble supports are described in U.S. Pat. Nos. 3,551,555, 3,553,310, 4,048,298 and RE-29,474, and by Tijssen (supra pp 297-328), for example. Procedures for binding of antibodies to polystyrene by adsorption are described in U.S. Pat. Nos. 3,646,346 and 4,092,408, for example.

A variety of materials can be used as the insoluble support, the primary consideration being the binding of the anti-(fetal restricted antigen) antibody or the anti-(adult antigen) antibody to the surface, the absence of interference with the reagent binding reaction or with other reactions which can be employed to determine the presence and extent of the binding reaction. Organic and inorganic polymers, both natural and synthetic, can be used as the insoluble support. Examples of suitable polymers include polyethylene, polypropylene, polybutylene, poly(4-methylbutylene), butyl rubber, silastic polymers, polyesters, polyamides, cellulose and cellulose derivatives (such as cellulose acetate, nitrocellulose and the like), acrylates, methacrylates, vinyl polymers (such as polyvinyl acetate, polyvinyl chloride, polyvinylidene chloride, polyvinyl fluoride, and the like), polystyrene and styrene graft copolymers, rayon, nylon, polyvinylbutyrate, polyformaldehyde, etc. Other materials which can be used as the insoluble support are the latexes of the above polymers, silica gel, silicon wafers, glass, paper, insoluble protein, metals, metalloids, metal oxides, magnetic materials, semi-conductive materials, cermets and the like. In addition are included substances which form gels, e.g. proteins such as gelatins, lipopolysaccharides, silicates, agarose, polyacrylamides or polymers which form several aqueous phases such as dextrans, polyalkylene glycols (alkyene with 2 to 3 carbon atoms) or surfactants, e.g. amphophilic compounds such as phospholipids, long chain (12-24 carbon atoms) alkyl ammonium salts, and the like.

The preferred support comprises a nylon or nitrocellulose membrane. An alternate diagnostic support is made from polystyrene, styrene copolymers such as styrene-acrylonitrile copolymers, or polyolefins such as polyethylene or polypropylene, and acrylate and methacrylate polymers and copolymers. The anti-(fetal restricted antigen) reagent antibody or the other antibody reagents can be bound to the insoluble support by adsorption, ionic bonding, van der Waals adsorption, electrostatic bonding, or other non-covalent bonding, or it can be bound to the insoluble support by covalent bonding. A particularly advantageous support for this procedure comprises a microtiter plate having a plurality of wells. The well surface or plastic cup inserts therein can constitute the antigen or antibody support. If the determination will require the use of fluorometric measurements, the microtiter plate or the well inserts are advantageously opaque to light so that excitation light applied to a well does not reach or influence contents of the surrounding wells.

Procedures for non-covalent bonding are described in U.S. Pat. No. 4,528,267. Procedures for covalently bonding antibodies and antigens to insoluble supports are described by Ichiro Chibata in IMMOBILIZED ENZYMES. Halsted Press: New York (1978) and A. Cuatrecasas, *J.Bio.Chem.* 245:3059 (1970), the entire contents of which are hereby incorporated by reference. The surface can be coated with a protein and coupled with the antibody or antigen using procedures described in U.S. Pat. No. 4,210,418 using glutaraldehyde as a coupling agent, for example. In a still further procedure, the well can be coated with a layer having free isocyanate groups such as a polyether isocyanate, and application of the antibody or antigen in aqueous solution thereto effects the requisite bonding. In a still further procedure, the antibody or antigen can be coupled to a hydroxylated material by means of cyanogen bromide as described in U.S. Pat. No. 3,720,760.

The insoluble supports are preferably "blocked" to reduce non-specific binding. The choice of suitable blocking agents in determined by the type of insoluble support. For example, for polystyrene supports, suitable blocking agents include water-soluble non-immune animal proteins. Suitable water-soluble non-immune animal proteins include bovine (BSA), human, rabbit, goat, sheep, and horse serum albumins; casein and non-fat milk; ovalbumin, glycoproteins, and the like.

The same blocking agents can also be used for nylon and nitrocellulose supports. However, a preferred blocking agent for nitrocellulose or nylon membrane supports is non-fat milk or casein. An optimum blocking agent for these membrane supports is an aqueous solution containing from 1 to 5 wt.% non-fat dried milk or casein, and nonionic surfactants such as polyoxyethylene sorbitan derivatives and polyoxyethylene ethers.

The labeled anti-(fetal restricted antigen) antibody, anti-(normal antigen) antibody and anti-(antibody) reagents of this invention can be prepared by conventional procedures for attaching labels to proteins, preferably with suitable protection of antibody binding sites. The labels can be bonded or coupled to the protein reagents by chemical or physical bonding. Ligands and groups which can be bound to the antibodies of this invention include elements, compounds or biological materials which have physical or chemical characteristics which can be used to distinguish the reagents to which they are bonded from compounds and materials in the sample being tested.

Radiolabeled anti-(fetal antigen) antibodies of this invention can be used for in vitro diagnostic tests. The specific activity of a tagged antibody depends upon the half-life, isotopic purity of the radioactive label and how the label is incorporated into the antigen or antibody. Table A lists several commonly used isotopes, their specific activities and half-lives. In immunoassay tests, the higher the specific activity, in general, the better the sensitivity.

TABLE A

| Isotope | Specific Activity of Pure Isotope (Curies/mole) | Half-Life |
|---|---|---|
| $^{14}C$ | $6.25 \times 10^1$ | 5720 years |
| $^{3}H$ | $2.91 \times 10^4$ | 12.5 years |
| $^{35}S$ | $1.50 \times 10^6$ | 87 days |
| $^{125}I$ | $2.18 \times 10^6$ | 60 days |
| $^{32}P$ | $3.16 \times 10^6$ | 14.3 days |
| $^{131}I$ | $1.62 \times 10^7$ | 8.1 days |

Procedures for labeling antibodies with radioactive isotopes listed in Table A are generally known in the art. Tritium labeling procedures are described in U.S. Pat. No. 4,302,438, for example. Iodinating, tritium labeling and $^{35}S$ labeling procedures especially adapted for antibodies are described by Goding (supra, pp 124–126), and the references cited therein. Other procedures for iodinating antibodies are described by Hunter and Greenwood, *Nature.* 144:945 (1962), by David et al, *Biochemistry.* 13:1014–1021 (1974), and in U.S. Pat. Nos. 3,867,517 and 4,376,110. Examples of suitable systems, coupling procedures and substrate reactions therewith are disclosed in U.S. Pat. Re. Nos. 31,006, B1 3,654,090, 4,214,048, 4,289,747, 4,302,438, 4,312,943, 4,376,110 and the references cited therein, for example. Examples of other suitable systems are described by Pesce et al, *Clin.Chem.* 20:353–359 (1974) and Wisdom, G., *Clin.- Chem.* 22:1243 (1976).

A list of suitable enzyme classes which can be used for labeling, and specific examples for each class, follow:

TABLE B

| Class | Enzyme Example |
|---|---|
| Hydrolases | Amylases |
| Nucelases | Polynucleotidase |
| Amidases | Arginase |
| Purine deaminases | Adenase |
| Peptidases | Aminopolypeptidase |
| Proteinases | Pepsin |
| Esterases | Lipases |
| Iron Enzymes | Catalase |
| Copper Enzymes | Tyrosinases |
| Enzymes containing Coenzymes | Alcohol dehydrogenase |
| Enzymes reducing cytochrome | Succinic dehydrogenase |
| Yellow enzymes | Diaphorase |
| Mutases | Glyoxalase |
| Desmolases | Aldolase |
| Oxidases | Glucose oxidase |
| | Horseradish peroxidase |
| Phosphatases | Alkaline Phosphatases |
| | Acid Phosphatases |
| Dehydrogenases | G6PDH (Glucose 6 phosphodehydrogenase) |
| β-galactosidase | |
| Phosphorylases | |
| Hexokinases | |

A list of suitable enzymes are described in Hawk, et al. PRACTICAL PHYSIOLOGICAL CHEMISTRY, New York: McGraw-Hill pp 306–397 (1954).

Fluorogenic and chromogenic enzymes (enzymes in the presence of which a selected substrate will produce a fluorescent or chromogenic product) are useful labeling moieties. Methods for selectively conjugating enzymes to antibodies without impairing the ability of the antibody to bind with antigen and for conjugating enzymes to proteinaceous reagents are well known in the art.

Suitable enzymes and procedures for coupling them to antibodies are described by Ichiro Chibata in IMMOBILIZED ENZYMES (supra); A. Cuatrecasas, *J.Bio.-Chem.* (supra); Wilson, M. et al., INTERNATIONAL CONFERENCE IN IMMUNOFLUORESCENCE AND RELATED STAINING TECHNIQUES. W. Knapp et al., editors. *Amsterdam;* Elsevier pp 215-244 (1978); Sullivan, M. et al., *Annals of Clinical Biochemistry.* 16:221-240 (1979); Nygren, H. et al., *Medical Biology.* 57:187-191 (1979); Gadkari, D. et al., *Journal of Virological Methods.* 10:215-224 (1985); Tijssen, P. et al., *Analytical Biochemistry.* 136:451-457 (1984); Tsuruta, J. et al., *The Journal of Histochemistry and Cytochemistry.* 33:767-777 (1985); Ishikawa, E., *Journal of Immunoassay.* 4:209-327 (1983); and in U.S. Pat. No. 4,190,496, for example, the entire contents of the above listed references being hereby incorporated by reference in their entireties.

The preferred enzymes and suitable substrates corresponding thereto include horseradish peroxidase for which suitable substrates are o-phenylenediamine, m-phenylenediamine, o-dianisidine, and 4-chloro-$\alpha$-napthol. They also include $\beta$-galactosidase for which suitable substrates are 4-methylumbelliferyl-$\beta$-D-galactoside, p-nitrophenyl-$\beta$-D-galactose, p-nitrophenol, o-nitrophenyl-$\beta$-D-galactose, and onitrophenol, for example. The include alkaline phosphatase for which suitable substrates are p-nitrophenylphosphate, indoxyl phosphate, and 5-bromo-3-chloroindoxyl phosphate, for example.

Examples of suitable procedures for enzyme labeling the antibody include the use of carbodiimides, dialdehydes, and gluteraldehyde bifunctional coupling reagents. Linkage of enzymes through amine groups can be achieved by treating the proteins with thionyl chloride, N-hydroxysuccinimide or similar reagents in an anhydrous solvent such as dimethylformamide, dioxane, dimethylsulfoxide, tetrahydrofuran, or the like. Alternative coupling agents include carbodiimides such as 1-ethyl-3-(3-(N,N'-dimethylamino)propyl)-carbodiimide, 1-cyclohexyl-3-(2-morpholinoethyl)carbodiimide methyl-p-toluenesulfonate, succinimidyl 4-(N-maleimidoethyl)-cyclohexane-1-carboxylate, and succinimidyl 3-(2-pyridyldithio)-propionate, for example.

The carbohydrate moiety of an enzyme can also be oxidized to an aldehyde and reacted with lysyl amino groups of immunoglobulins to form a Schiff's base. Reduction with sodium borohydride effects a stable linkage of enzyme and antibody. Horseradish peroxidase with antibody can be efficiently linked to immunoglobulins by the method of Wilson, supra.

Fluorophore and chromophore labeled antibodies can be prepared from standard moieties known in the art. Since antibodies and other proteins absorb light having wavelengths up to about 310 nm, the fluorescent moieties should be selected to have substantial absorption at wavelengths above 310 nm and preferably above 400 nm. A variety of suitable fluorescers and chromophores are described by Stryer, Science, 162:526 (1968) and Brand, L. et al, *Annual Review of Biochemistry.* 41:843-868 (1972). The antibodies can be labeled with fluorescent chromophore groups by conventional procedures such as those disclosed in U.S. Pat. Nos. 3,940,475, 4,289,747 and 4,376,110, for example.

One group of fluorescers having a number of the desirable properties described above are the xanthene dyes, which include the fluoresceins derived from 3,6-dihydroxy-9-phenylxanthhydrol and resamines and rhodamines derived from 3,6-diamino-9-phenylxanthydrol and lissanime rhodamine B. The rhodamine and fluorescein derivatives of 9-o-carboxyphenylxanthhydrol have a 9-o-carboxyphenyl group. Fluorescein compounds having reactive coupling groups such as amino and isothiocyanate groups such as fluorescein isothiocyanate and fluorescamine are readily available. Another group of fluorescent compounds are the naphthylamines, having an amino group in the $\alpha$ or $\beta$ position.

Antibodies can be labeled with fluorochromes or chromophores by the procedures described by Goding, J. (supra, pp 208-249).

The antibodies used in the methods of this invention can be covalently bonded to avidin or biotin in one embodiment of this invention. Suitable binding procedures involve cross-linking through a bifunctional cross-linking agent. Suitable bifunctional compounds are described by Peters, K. et al, *Ann.Rev.Biochim.* 46:523 (1977).

In other instances, the bonds can be formed directly between the reagents themselves. For example, antibody can be bound to avidin through functional groups on the respective materials. As a specific example, avidin can be treated with periodate and reacted with antibody to give a Schiff base formation without inhibiting the biotin to avidin binding or blocking immuological activity of the antibody.

Known techniques using bifunctional cross-linking agents include the following: (a) a one-step glutaraldehyde linkage, Avrameas, S., Immunochemistry. 6:43 (1969); (b) two-step glutaraldehyde linkage, *Avrameas, S., Immunochemistry.* 8:1175 (1971); and (c) dimaleimide linkage, Kato, K. et al, *Euro.J.Biochem.* 62:285 (1966).

Antibodies can be labeled with metallic radionuclides according the procedure of Hnatowich, D. et al. *Journal of Applied Radiation.* 35:554-557 (1984) and Buckley, R. et al. *Federation of European Biochemical Societies.* 166:202-204 (Jan. 1984).

One embodiment of the immunoassay methods of this invention uses an insoluble support such as a polystyrene plate to which anti-(fetal restricted antigen) antibody is adhered, either directly or through a goat anti-mouse antibody. It is contacted with a sample diluted with an aqueous buffer solution such as phosphate buffer solution (PBS), pH 6 to 8 and preferably from 7.2 to 7.6 for a sufficient time to permit binding of fetal restricted antigen in the sample with the anti-(fetal restricted antigen) antibody on the insoluble support, and then removing the sample from the support. The incubation time should be sufficient to permit substantial binding to occur, the time being temperature dependent. Suitable incubation times are from 30 to 240 minutes at temperatures within the range of from 16° to 40° C., the preferred contact time being at least 60 minutes at temperatures within the range of from 20° to 26° C. The residual sample solution is then removed from the support by use of a rinse solution. Any conventional rinse solution can be used. A suitable rinse solution is described in U.S. Pat. No. 4,528,267. It is an aqueous phosphate buffer solution having a phosphate molarity of from 0.0001 to 0.05, a pH of from 6 to 8 and containing from 0.001 to 0.1 weight percent of non-ionic surfactant. Suitable non-ionic surfactants include polyoxyethylene ethers (BRIJ such as lauryl, cetyl, oleyl, stearyl, and tridecyl polyoxyethylene ethers); polyoxyethylene sorbitans (TWEEN such as polyoxyethylene sorbital monolaurate, monopalmitate, monostearate, monoleate, and trioleates); and other polyoxyethylene ethers (TRITON, for example).

The insoluble support is then contacted with a secondary antibody which will bind with the captured fetal restricted antigen on the insoluble support, the sandwiching antibody. The sandwiching antibody can be labeled or unlabeled. In the event that an unlabeled sandwiching antibody is used, a tertiary antibody which binds with the sandwiching antibody and which bears a physically detectable label can be used in a conventional manner to determine the sandwiching antibody.

A variety of labels have been described above. For purposes of clarity and not by way of limitation, the subsequent steps of the process will be described for anti-(adult antigen) antibodies which have been labeled with an enzyme, preferably a chromogenic or a fluorogenic enzyme. The term "chromogenic enzyme" is defined herein to refer to an enzyme which will produce a chromophore product with a suitable substrate. The term "fluorogenic enzyme" is defined herein to refer to an enzyme which will produce a fluorophore product with a suitable substrate.

The sandwiching antibody is applied to the insoluble support in an aqueous solution. The solution preferably contains suitable salts and buffers to preserve the reactants and facilitate the binding reaction. For example, the solution can contain bovine serum albumin (BSA), phosphate buffer solution (PBS), and a mild surfactant such as polyoxyethylene sorbitan ester employed in the above-described rinse solution. The incubation is continued for sufficient time to permit the sandwiching antibody to bind with exposed fetal restricted antigen epitopes, if any, adhering to the insoluble support. The preferred incubation times and temperatures are as set forth for the binding of insolubilized reagent anti-(fetal antigen) antibody with the mucus fetal antigen (or complex thereof).

The sandwiching antibody solution is then removed from the insoluble support, and the support is rinsed with a rinse solution such as described above, to remove any residual, unbound labeled material.

If the sandwiching antibody is unlabeled, an enzyme labeled antibody or other binding agent which binds selectively with the sandwiching antibody is applied to the insoluble support in an aqueous solution. The solution preferably contains suitable salts and buffers to preserve the reactants and facilitate the binding reaction. For example, the solution can contain bovine serum albumin (BSA), phosphate buffer solution (PBS), and a mild surfactant such as polyoxyethylene sorbitan ester employed in the above-described rinse solution. The incubation is continued for sufficient time to permit labeled anti-(adult antigen) antibody to bind with exposed fetal antigen epitopes, if any, adhering to the insoluble support. The preferred incubation times and temperatures are as set forth for the binding of insolubilized reagent anti-(fetal antigen) antibody with the mucus fetal antigen (or complex thereof).

The labeled antibody solution is then removed from the insoluble support, and the support is rinsed with a rinse solution such as described above, to remove any residual, unbound labeled material.

In a next step of the sandwich process of this invention, the insoluble support is contacted with an aqueous solution of a substrate which undergoes a reaction in the presence of the enzyme to release fluorescent or chromogen compound into the solution. Suitable substrates and the enzymes which which they can be converted are described in U.S. Pat. Nos. 4,190,496 and 4,528,267, for example. The support is contacted with an aqueous solution of the substrate containing from $10^{-2}$ to $10^{-10}$ molar concentrations of the substrate. Substrate molar concentrations of from $10^{-4}$ to $10^{-5}$ are preferred. Preferred additional reagents and buffers in the substrate solution include 2-amino-2-methyl-1-propanol buffer, TRIS, and magnesium chloride, for example.

The substrate solution is incubated with the insoluble support for sufficient time for the reaction yielding the fluorophore or chromophore to occur. At temperatures of from 18° to 40° C., incubation times of from 5 to 240 minutes can be used. Preferably, the temperature is within the range of from 20° to 26° C., and the incubation time is from 30 to 120 minutes.

The fluorescent or chromophore level in the solution is then measured. The equipment and procedures for determining the level of fluorescence or chromophore level in the substrate solutions are those conventionally used in the art. The level of fluorescence or chromogen in solution is a function of the enzyme concentration on the insoluble support which is, in turn, a function of the amount of fetal antigen in the mucus sample. The concentration of the fetal antigen can be determined by comparing the fluorescence or chromophore level of the solution with respective fluorescence or chromophore levels obtained with control solutions containing known concentrations of fetal antigen.

In a membrane embodiment of the immunoassay methods of this invention, an insoluble support to which anti-(adult plasma fibronectin) antibody is adhered is contacted with a cervical mucus sample diluted with an aqueous buffer solution such as phosphate buffer solution (PBS), pH 6 to 8 and preferably from 7.2 to 7.6 for a sufficient time to permit binding of fetal restricted antigen in the sample with the anti-(fetal restricted antigen) antibody on the insoluble support. The time required for binding is very small in a flow through system. Suitable incubation times can be one sec up to 20 min at temperatures within the range of from 16° to 40° C., the preferred contact time being less than one min and optimally from 10 sec to 2 min.

The insoluble support is then contacted with an antibody which will bind with the captured fetal restricted antigen on the insoluble support, the sandwiching antibody. The sandwiching antibody can be labeled or unlabeled. In the event that an unlabeled sandwiching antibody is used, a secondary antibody which binds with the sandwiching antibody and which bears a physically detectable label can be used in a conventional manner to determine the sandwiching antibody.

A variety of labels have been described above. For purposes of clarity and not by way of limitation, the subsequent steps of the process will be described for anti-(fetal antigen) antibodies which have been labeled with an enzyme, preferably a chromogenic enzyme.

The sandwiching antibody is applied to the insoluble support in an aqueous solution. The solution preferably contains suitable salts and buffers to preserve the reactants and facilitate the binding reaction. For example, the solution can contain bovine serum albumin (BSA), phosphate buffer solution (PBS), and a mild surfactant such as polyoxyethylene sorbitan ester employed in the above-described rinse solution. The incubation is continued for sufficient time to permit the sandwiching antibody to bind with exposed fetal restricted antigen epitopes, if any, adhering to the insoluble support. The preferred incubation times and temperatures are as set forth for the binding of insolubilized reagent anti-(fetal antigen) antibody with the mucus fetal antigen (or complex thereof).

The sandwiching antibody solution optionally can be removed from the insoluble support, and the support is rinsed with a rinse solution such as described above, to remove any residual, unbound labeled material.

If the sandwiching antibody is unlabeled, an enzyme labeled antibody or other binding agent which binds selectively with the sandwiching antibody is applied to the insoluble support in an aqueous solution. The solution preferably contains suitable salts and buffers to preserve the reactants and facilitate the binding reaction. For example, the solution can contain bovine serum albumin (BSA), phosphate buffer solution (PBS), and a mild surfactant such as polyoxyethylene sorbitan ester employed in the above-described rinse solution. The incubation is continued for sufficient time to permit labeled anti-(fetal antigen) antibody to bind with exposed fetal antigen epitopes, if any, adhering to the insoluble support. The preferred incubation times and temperatures are as set forth for the binding of insolubilized reagent anti-(fetal antigen) antibody with the fetal antigen (or complex thereof).

The labeled antibody solution is then removed from the insoluble support, and the support is rinsed with a rinse solution such as described above, to remove any residual, unbound labeled material.

In a next step of the sandwich process of this invention, the insoluble support is contacted with an aqueous solution of a substrate which undergoes a reaction in the presence of the enzyme to release chromogen compound into the solution. Suitable substrates and the enzymes which which they can be converted are described in U.S. Pat. Nos. 4,190,496 and 4,528,267, for example. The support is contacted with an aqueous solution of the substrate containing from $10^{-2}$ to $10^{-10}$ molar concentrations of the substrate. Preferred additional reagents and buffers in the substrate solution include 2-amino-2-methyl-1-propanol buffer, TRIS, and magnesium chloride, for example.

The substrate solution is incubated with the insoluble support for sufficient time for the reaction yielding the fluorophore or chromophore to occur. At temperatures of from 18° to 40° C., incubation times of from 1 to 20 min can be used. Preferably, the temperature is within the range of from 20° to 26° C., and the incubation time is from 2 to 5 min. The chromogen level on the membrane can be measured using a reflectometer or densitometer.

The kits of this invention comprise combinations of buffers for transport and storage with sampling devices such as sampling swabs; supports having reagents of this invention adhered thereto; vials, foil packages or other containers of reagents of this invention; and combinations thereof. Each of the insoluble support structures in a foil package can be combined with other reagents in vials or other packages. They can also be combined with other, optional reagents such as stop reagents in separate vials or other packages.

This invention is further illustrated by the following specific, but non-limiting examples. Temperatures are given in degrees Centigrade and percents as weight percents unless otherwise specified. Examples which are constructively reduced to practice herein are presented in the present tense, and examples representing laboratory experiments previously reduced to practice are presented in the past tense.

EXAMPLE 1

Polyclonal Anti-(fetal fibronectin) Antibodies

Fetal fibronectin is purified from amniotic fluid as described by Engvall and Ruoslahti, *Int.J.Cancer.* 20:1–5 (1977).

The anti-(fetal fibronectin) antibodies are elicited in rabbits using the immunization techniques and schedules described in the literature, e.g., Stollar, *Methods of Enzymology.* 70:70 (1980), immunizing the rabbits with the fetal fibronectin antigen. The antiserum is screened in a solid phase assay similar to that used for monoclonal antibodies, e.g., as described by Lange et al, *Clin.Exp.Immunol.* 25:191 (1976) and Pisetsky et al, *J.Immun.Methods* 41:187 (1981).

The IgG fraction of the antisera is purified further by affinity chromatography using CNBr-Sepharose 4B (Pharmacia Fine Chemicals) to which has been coupled fetal fibronectin. The method used for coupling is that recommended by the gel manufacturer, AFFINITY CHROMATOGRAPHY. Pharmacia Fine Chemicals, pp 15–18.

The column is equilibrated with from 2 to 3 volumes of buffer (0.01 M PBS, pH 7.2), and the anti-(fetal fibronectin) antibody containing solution is then applied to the column. The absorbency of the eluate is monitored at 280 nm until protein no longer passes from the column. The column is then washed with 0.1 M glycine buffer, pH 2.5, to desorb the immunoaffinity bound anti-fetal fibronectin antibody. Peak protein fractions are collected, pooled and dialyzed against 0.01 M PBS, pH 7.2, for 24–36 hr at 4° C. with multiple buffer changes.

If a higher purity is desired, the affinity purified IgG can be passed through an adult plasma fibronectin bound affinity column by the procedure described above to remove any antibodies which would cross-react with adult plasma fibronectins.

EXAMPLE 2

Monoclonal Anti-(fetal antigen) Antibody

Using the purified fetal fibronectin obtained by the procedure of Example 1, mouse monoclonal antibodies to the fetal fibronectin are obtained using standard procedures of Galfre and Milstein, *Methods in Enzym.* 73:1 (1981) and Matsurra, H. and Hakomori, S. et al (supra), using fetal fibronectin as the antigen for immunizing the mice. The monoclonal antibodies are screened using a modification of the techniques described in the literature, e.g., Lange et al, Clin.Exp.Immunol. 25:191 (1976) and Pisetsky et al, *J.Immun.Methods.* 41:187 (1981).

Mouse monoclonal antibody is purified from ascites fluid or from hybridoma culture supernatants using Protein-A coupled Sepharose-4B (Pharmacia Fine Chemicals) according to the procedure of Tijsson, PRACTICE AND THEORY OF ENZYME IMMUNOASSAYS. Elsevier Science Publishers, pp 105–107 (1985).

EXAMPLE 3

Polyclonal Antibody Coated Microtiter Plate

Rabbit anti-(fetal fibronectin) prepared and further purified to remove adult fibronectin cross-reactivity as described in Example 1 is diluted to 10 μg/mL in 0.05 M carbonate buffer, pH 9.6. 100 μL is dispersed into each well of of an IMMULON II microtiter plate (Dynatech). The plate is covered and incubated 4 hr at room temperature or 4° C. overnight. The plate is washed 4 times with Wash Buffer (0.02 M Tris HCl, 0.015 M NaCl, 0.05% TWEEN-20), filling and emptying the wells completely with each use. The plate is then blocked by dispersing into each well 200 μL of a blocking solution (0.01 M PBS, 1% BSA, 0.02% NaN$_3$, pH 7.4) and incubating for 1 hr at room temperature. The wells are then washed 4 times with Wash Buffer, as described above. The plate is now ready for immunoassay of samples.

EXAMPLE 4

Monoclonal Anitbody Coated Micotiter Plate

Goat F(ab')$_2$ anti-mouse IgG antibody (Tago) was diluted to 10 μg/mL in 0.05 M carbonate buffer, pH 9.6. 100 μL was dispersed into each well of an IMMULON II microtiter plate (Dynatech). The plate was covered and incubated 4 hr at room temperature or 4° C. overnight. The plate was washed 4 times with Wash Buffer as described in Example 3. The plate was then blocked by dispensing into each well the Blocking Solution as described in Example 3. Mouse monoclonal anti-fetal fibronectin ascites prepared as in Example 2 was diluted 1/5000 with 0.01 M PBS-1% BSA, pH 7.4. 100 μL of the solution was dispensed into each well of the blocked microtiter plate. The wells were incubated, covered, for 2 hr at room temperature or overnight at 4° C. The plate was then washed 4 times with Wash Buffer as described above, and was then ready for immunoassay of samples.

EXAMPLE 5

Enzyme Labeled Anti-(fetal fibronectin) Antibody

Anti-(fetal antigen) antibody prepared in accordance with the procedures of Example 1 or Example 2 is conjugated with alkaline phosphatase following the one-step glutaraldehyde procedure Avrameas, *Immunochemistry.* 6:43 (1969).

EXAMPLE 6

Sandwich Immunoassay

Positive and negative controls were included in the test. The positive control was amniotic fluid of know fetal fibronectin concentration, appropriately diluted to fall within the assay range (20 ng/mL to 5 μg/mL for a monoclonal based assay). The negative control was sample diluent. The Assay Standard was amniotic fluid of known fibronectin concentration, serially diluted in sample diluent to provide a standard curve, ranging from 20 ng to 5μg/mL.

The sample diluent was the anti-protease cocktail described in U.S. Pat. No. 4,914,889, the entire contents of which are hereby incorporated by reference. It protects fibronectin-containing samples from proteolytic degradation during transit and storage. The solution consisted of 0.05 M Tris-HCl, pH 7.4; 0.15 M NaCl, 0.02% NaN$_3$, 1% BSA, 500 Kallikrein Units/mL of aprotinin, 1nM phenylmethylsulfonyl fluoride (PMSF) and 5 mM EDTA.

Swab samples collected from either the cervix or posterior fornix were immersed in 0.75 mL of sample diluent in a collection vial. The swabs were removed from the solution for the assay, and the solution was centrifuged at 13,000 rpm for 5 min to remove particulate. The supernatant contained any fetal fibronectin which was in the swab.

A microtiter plate prepared as in Example 3 or 4 is used for the assay. 100 μL of each standard, sample, positive and negative control were placed in separate wells and incubated 2 hr at room temperature. The plate was washed 4 times with Wash Buffer as described in Examples 3 and 4. 100 μL of alkaline phosphatase-conjugated goat anti-(human fibronectin) prepared as in Example 5 was diluted 1/1000 in Conjugate Buffer (0.02 M Tris-HCl, pH 8, 0.3 M NaCl, 0.05% TWEEN 20, 5% BSA, 0.02% NaN$_3$). 100 μL was dispensed into each well and incubated for 2 hr at room temperature. The plate was washed 4 times as previously described. 4 mg/mL of p-nitrophenylphosphate (PNPP) was used as the substrate. This was diluted in 0.18 M 2-amino-2-methyl-1-propanol (AMP) buffer, pH 9.5 with 0.12 mM MgCl$_2$. 100 μL was dispensed into each well of the microtiter plate. After a 5 min incubation at room temperature, the reaction rate in milli-OD/min was read at 405 nm on a V-MAX ™ kinetic microtiter plate reader (Molecular Devices).

A standard curve was constructed by correlating increasing reaction rate with increasing fibronectin concentration in the standards. Unknowns were calculated directly from the curve or by using a pre-set computer program (Molecular Devices).

We claim:

1. A method for determining signs and symptoms indicating risk of delivery comprising
   a) obtaining a secretion sample from the vaginal cavity or the cervical canal for a pregnant patient after week 20 of pregnancy; and
   b) determining the presence of fetal fibronectin in the sample, the presence of fetal fibronectin in the sample indicating risk of delivery.

2. The method of claim 1 wherein the sample is removed from the posterior fornix.

3. The method of claim 1 wherein the sample is obtained from the cervical os.

4. The method of claim 1 comprising the steps of
   a) contacting diluted sample with an anti-(fetal fibronectin) antibody for a time sufficient to permit antigen-antibody binding to occur; and
   b) determining the presence of said binding.

5. He method of claim 4 comprising the steps of
   a) contacting the sample with an insoluble support to which anti-(fetal fibronectin) antibody is adhered for a time sufficient to permit antigen-antibody binding to occur;
   b) contacting the insoluble support with an anti-fibronectin antibody for a time sufficient to permit antigen-antibody binding to occur; and
   c) determining the presence of anti-fibronectin antibody on the insoluble support.

6. The method of claim 5 wherein the anti-fibronectin antibody has a physically detectable label.

7. The method of claim 5 wherein the presence of anti-fibronectin antibody is determined by a) contacting the insoluble support with a labeled antibody which binds selectively with the anti-fibronectin antibody; and b) determining the presence of the label on the insoluble support.

8. He method of claim 1 comprising the steps of a) contacting the sample with an insoluble support to which anti-fibronectin antibody is adhered for a time sufficient to permit antigen-antibody binding to occur;

b) contacting the insoluble support with an anti-(fetal fibronectin) antibody for a time sufficient to permit antigen-antibody binding to occur; and c) determining the presence of anti-(fetal fibronectin) antibody on the insoluble support.

9. The method of claim 8 wherein the anti-(fetal fibronectin) antibody has a physically detectable label.

10. The method of claim 8 wherein the presence of anti-(fetal fibronectin) antibody is determined by a) contacting the insoluble support with a labelled antibody which binds selectively with the anti-(fetal fibronectin) antibody; and b) determining the presence of the label on the insoluble support.

11. The method of claim 1 wherein said method determines labor.

12. The method of claim 1 wherein said method determines fetal membrane rupture.

13. The method of claim 1 wherein said pregnant patient is a preterm patient.

14. The method of claim 1 wherein said pregnant patient is a term patient.

* * * * *

UNITED STATES PATENT AND TRADEMARK OFFICE
CERTIFICATE OF CORRECTION

PATENT NO. : 5,096,830
DATED : March 17, 1992
INVENTOR(S) : Senyei, Andrew E. and Teng, Nelson N.H.

It is certified that error appears in the above-indentified patent and that said Letters Patent is hereby corrected as shown below:

On title page, item [54] in title and col. 1, lines 1-2 should read
--LABOR AND MEMBRANE RUPTURE TEST--
On title page, item [56] References Cited, "Int.J. Caner" should read
--Int. J. Cancer--
Column 11, line 35, delete "The" and insert --They--
Column 18, line 54, delete "He" and insert --The--
Column 19, line 8, delete "He" and insert --The--

Signed and Sealed this

Eighth Day of February, 1994

Attest:

BRUCE LEHMAN

*Attesting Officer*  *Commissioner of Patents and Trademarks*